(12) United States Patent
Fujiwara et al.

(10) Patent No.: US 9,704,475 B2
(45) Date of Patent: Jul. 11, 2017

(54) PLEASANT SOUND MAKING DEVICE FOR FACILITY APPARATUS SOUND, AND PLEASANT SOUND MAKING METHOD FOR FACILITY APPARATUS SOUND

(75) Inventors: Susumu Fujiwara, Tokyo (JP); Reiji Morioka, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 39 days.

(21) Appl. No.: 14/416,318

(22) PCT Filed: Sep. 6, 2012

(86) PCT No.: PCT/JP2012/072674
§ 371 (c)(1),
(2), (4) Date: Jan. 22, 2015

(87) PCT Pub. No.: WO2014/038029
PCT Pub. Date: Mar. 13, 2014

(65) Prior Publication Data
US 2015/0179161 A1   Jun. 25, 2015

(51) Int. Cl.
  *H03G 5/00* (2006.01)
  *G10K 15/04* (2006.01)
  *G10K 11/175* (2006.01)
  *A61M 21/02* (2006.01)
  (Continued)

(52) U.S. Cl.
CPC ............. *G10K 15/04* (2013.01); *A61M 21/02* (2013.01); *G10K 11/175* (2013.01); *A61M 2021/0027* (2013.01); *A61M 2230/06* (2013.01); *F24F 2011/0065* (2013.01)

(58) Field of Classification Search
USPC .... 381/98, 73.1, 91, 92, 101, 104, 105, 106, 381/109, 71.14, 71.11, 56, 402
See application file for complete search history.

(56) References Cited

U.S. PATENT DOCUMENTS

| 7,181,021 B2 * | 2/2007 | Raptopoulos ........ G10K 11/175 381/103 |
| 2012/0289848 A1 * | 11/2012 | Li ........................... A61B 7/00 600/528 |

FOREIGN PATENT DOCUMENTS

| JP | H04-369342 A | 12/1992 |
| JP | H05-257509 A | 10/1993 |
| JP | 2967400 B2 | 8/1999 |

(Continued)

OTHER PUBLICATIONS

International Search Report of the International Searching Authority mailed Dec. 11, 2012 for the corresponding international application No. PCT/JP2012/072674 (and English translation).

(Continued)

*Primary Examiner* — Yosef K Laekemariam
(74) *Attorney, Agent, or Firm* — Posz Law Group, PLC

(57) ABSTRACT

A pleasant sound making device processes temporal variation characteristics in nature such that a frequency component and a peak frequency component in a frequency band which coincide with or are approximate to a housing of an indoor unit provided with a driving part (a fan, a motor, etc.) do not coincide with or are not approximate to the housing, on the basis of subjective view and physiological response evaluations of humans, and operates the driving part with a signal based on the processed waveform.

17 Claims, 6 Drawing Sheets

(51) Int. Cl.
   *F24F 11/00*     (2006.01)
   *A61M 21/00*     (2006.01)

(56)              References Cited

FOREIGN PATENT DOCUMENTS

JP         2004-003791 A      1/2004
JP         2012-037577 A      2/2012
JP         2012-145615 A      8/2012

OTHER PUBLICATIONS

Extended European Search Report dated Jul. 5, 2016 issued in corresponding EP patent application No. 12884124.4.
Chinese Office Action of Oct. 28, 2016 in the corresponding CN application No. 201280075669.6(English translation attached).
Office Action dated Mar. 2, 2017 issued in corresponding CN patent application No. 201280075669.6 (and English translation).

* cited by examiner

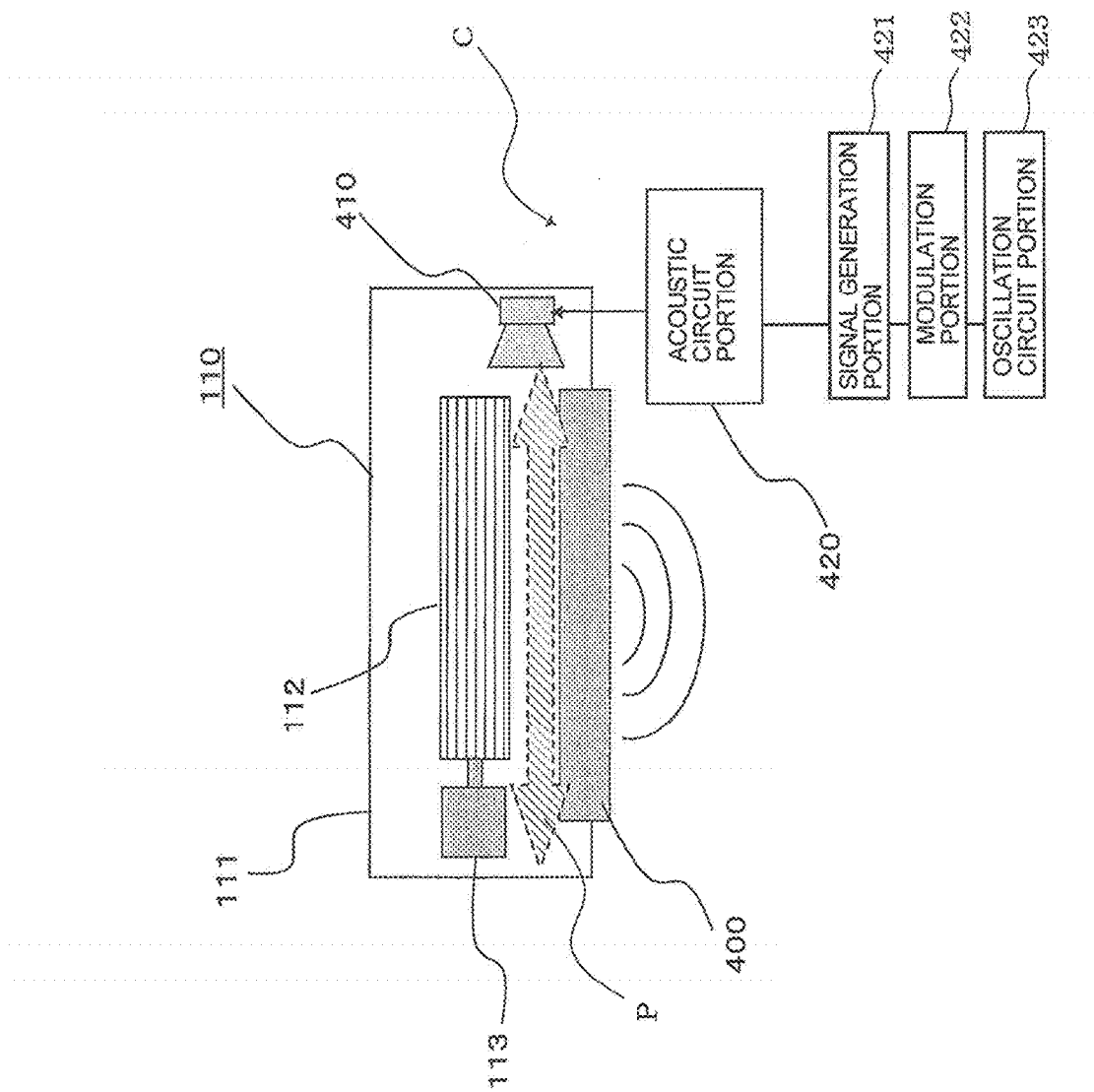

PLEASANT SOUND MAKING DEVICE FOR FACILITY APPARATUS SOUND, AND PLEASANT SOUND MAKING METHOD FOR FACILITY APPARATUS SOUND

CROSS REFERENCE TO RELATED APPLICATION

This application is a U.S. national stage application of International Application No. PCT/JP2012/072674 filed on Sep. 6, 2012, the disclosure of which is incorporated by reference.

TECHNICAL FIELD

The present invention relates to a pleasant sound making device for a facility apparatus sound, and a pleasant sound making method for a facility apparatus sound which are able to make a vibration sound (noise) generated by a facility apparatus (e.g., a home electrical appliance) into a pleasant sound.

BACKGROUND ART

Hitherto, various techniques to make a vibration sound (noise) generated by a home electrical appliance into a pleasant sound have been proposed. As such a technique, means is disclosed in which an unpleasant sound is masked by adding a sound having a bandwidth based on calculation of a critical bandwidth with respect to a specific frequency of a frequency component of an unpleasant sound (see, e.g., Patent Literature 1).

In addition, means is disclosed in which dedicated contents such as music are stored in electrical storage means, unpleasant sounds are collected as electrical signals, and then the dedicated contents are emitted by a speaker or the like such that unpleasant sounds are difficult to hear (see, e.g., Patent Literature 2).

CITATION LIST

Patent Literature

Patent Literature 1: Japanese Patent No. 2967400 (Example 1, etc.)
Patent Literature 2: Japanese Unexamined Patent Application Publication No. 2012-37577 (Example 3, etc.)

SUMMARY OF INVENTION

Technical Problem

The techniques described in Patent Literature 1 and 2, in which an unpleasant sound is masked to be made into a pleasant sound, have a problem with sound amplification or the like in unsteady signal variation since a sound phase component or the like is not actually considered. In addition, since the techniques do not take measures based on results of physiological responses of an unspecified number of humans, the techniques have a problem that a sound used for masking itself increases the degree of unpleasantness, or a pleasant feeling is not obtained. More specifically, the techniques have the following problems.

(1) Attention is required in artificially generating a sound which is not unpleasant, producing a content which does not cause a copyright problem, or the like.

(2) There is a possibility that the phase of a sound to be added to eliminate unpleasantness may coincide with that of noise and thus a sound source to be added becomes a second noise source.

(3) Due to an artificial sound source which almost does not consider a physiological response or the like of humans, an unpleasant feeling for a sound to be added may occur.

(4) Installation or the like of a microphone or the like having high stability is required for collecting noise signals for performing high-accuracy real-time processing, and a high-accuracy circuit is also required. Thus, the cost is low as compared to active noise control (ANC) or the like, but when a circuit configuration including a peripheral circuit required for signal processing is constructed, this results in a high cost demand.

(5) When high-accuracy signal processing is performed to emit a sound which reduces an unpleasant feeling, sound emission means such as a speaker obtained by dedicated acoustic design is required, and for a home electrical appliance, cost and spatial environment which are enough to allow a high-performance speaker unit to be installed are not present.

The present invention has been made in order to deal with the problems described above, and has as its object to provide a pleasant sound making device for a facility apparatus sound and a pleasant sound making method for a facility apparatus sound which make a vibration sound (noise) generated by a home electrical appliance into a pleasant sound on the basis of subjective view and physiological response evaluations of a live person.

Solution to Problem

A pleasant sound making device for a facility apparatus sound according to the present invention is a pleasant sound making device which makes a sound generated by an apparatus which operates a driving part, into a pleasant sound by using a temporal variation characteristic of a frequency of a sound generated in nature. The pleasant sound making device: performs filter processing so as to suppress a portion of a frequency component of the temporal variation characteristic of the frequency of the sound generated in nature, which coincides with or is approximate to an eigenvalue of a housing of the device provided with the driving part; evaluates a signal based on the variation characteristic after the filter processing, based on a subjective view and physiological response of humans with respect to a sound generated in nature when the driving part is operated; and selects the signal based on the variation characteristic after the filter processing, based on evaluation results of the subjective view and physiological response of the humans, and generates an operation signal for the driving part based on the selected signal.

A pleasant sound making method for a facility apparatus sound according to the present invention is a pleasant sound making method for making a sound generated by an apparatus which operates a driving part, into a pleasant sound by using a temporal variation characteristic of a frequency of a sound generated in nature. The pleasant sound making method includes: suppressing and processing a portion of a frequency component of the temporal variation characteristic of the frequency of the sound generated in nature, which coincides with or is approximate to an eigenvalue of a housing of the device provided with the driving part; evaluating a signal based on the processed variation characteristic of the frequency, based on a subjective view and physiological response of humans with respect to a sound generated in nature when the driving part is operated; selecting the signal based on the processed variation characteristic based on evaluation results of the subjective view and physiological response of the humans; generating an operation signal for the driving part based on the selected signal; and emitting, as an additional sound source, a sound obtained in advance by adjusting a sound pressure level and a period of the sound in nature with an average heart rate of a human.

Advantageous Effects of Invention

With the pleasant sound making device for a facility apparatus according to the present invention, it is possible to operate the driving part such as a motor, a fan, or the like with the "pleasant sound making waveform" generated on the basis of the evaluation results of a subjective view and physiological response of users. Thus, with the pleasant sound making device for a facility apparatus according to the present invention, it is possible to generate an acoustic characteristic which is determined as "pleasant" by humans.

With the pleasant sound making method for a facility apparatus according to the present invention, it is possible not only to generate an acoustic characteristic which is determined as "pleasant" by a human but also to perform a countermeasure against a housing vibration sound, and sleep induction, cool feeling adjustment, and warm feeling adjustment using a change in acoustic characteristic in time axis level.

BRIEF DESCRIPTION OF DRAWINGS

FIG. 6 is a schematic diagram for explaining an outline of a pleasant sound making device for a facility apparatus sound according to Embodiment 3 of the present invention.

DESCRIPTION OF EMBODIMENTS

Figure 1:
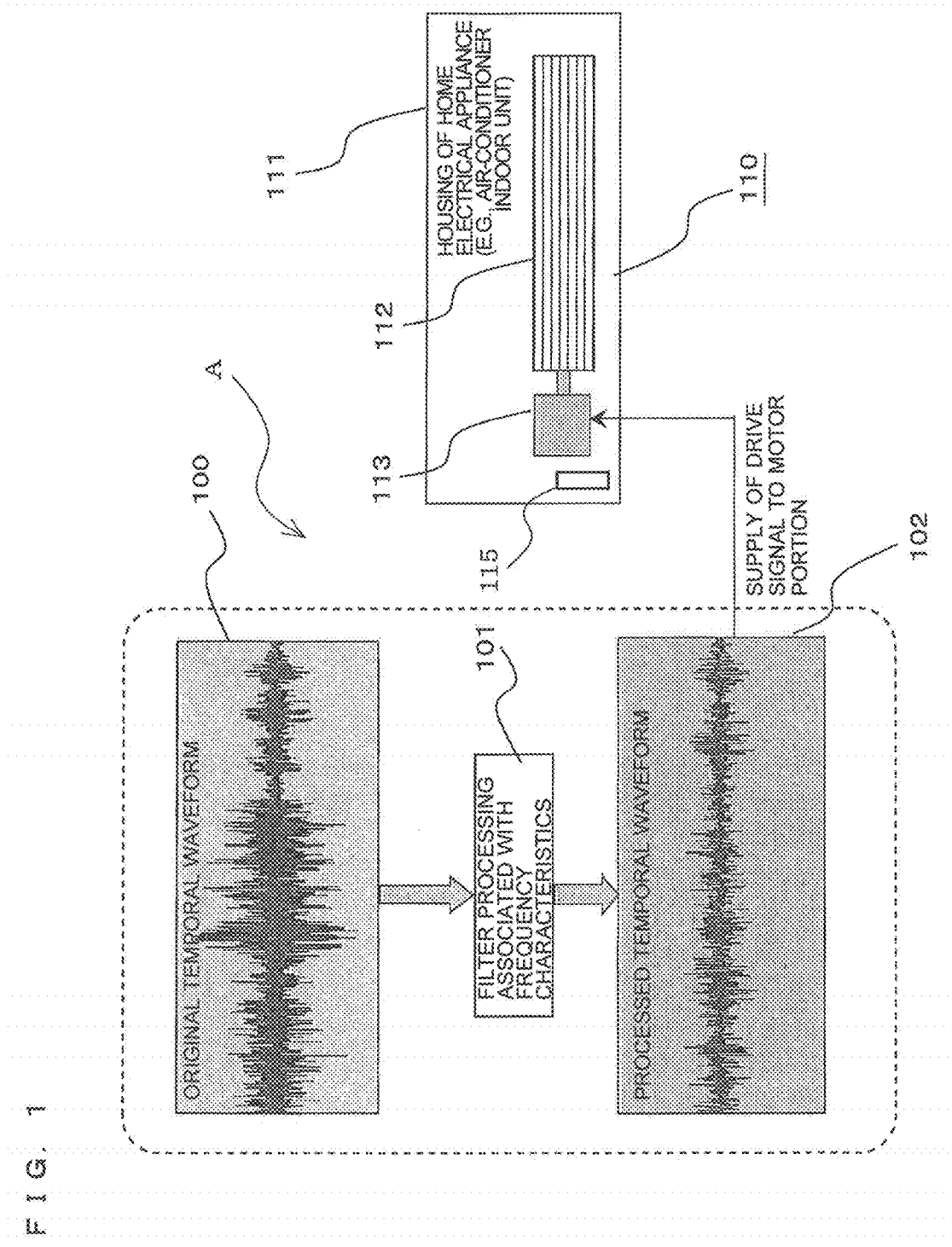
FIG. 1 is a schematic diagram for explaining an outline of a pleasant sound making device for a facility apparatus sound according to Embodiment 1 of the present invention.

Embodiments of the present invention will be described hereinafter with reference to the accompanying drawings. Note that the relationship of the size of each constituent element in the drawings described below including FIG. 1 may be different from actual size. In addition, in the drawings described below including FIG. 1, the same reference numerals denote the same or equivalent components, and this is common throughout the specification. Furthermore, the form of each constituent element represented throughout the specification is merely illustrative and is not limited to these descriptions.

Embodiment 1

FIG. 1 is a schematic diagram for explaining an outline of a pleasant sound making device for a facility apparatus sound (to be simply referred to as a pleasant sound making device A hereinafter) according to Embodiment 1 of the present invention. A case where the pleasant sound making device A is used in an indoor unit 110 of an air-conditioning apparatus which exemplifies a facility apparatus will be described herein as an example. The pleasant sound making device A is used in a facility apparatus which rotates a driving part such as a motor, a fan, or the like with a periodic signal and an unsteady signal using temporal variation characteristics in nature, and the driving part is operated with a "pleasant sound making waveform" based on subjective view and physiological response evaluations of live persons (users), thereby making an unpleasant sound into a pleasant sound.

The pleasant sound making device A has stored a time axis-input voltage waveform example 100 of a sound in nature (to be referred to as a nature waveform example 100 hereinafter). In addition, the pleasant sound making device A includes a filter processing unit 101 which performs filter processing of the nature waveform example 100 associated with frequency characteristics. Furthermore, the pleasant sound making device A is able to store a time axis-input voltage waveform example 102 obtained as a result of the filter processing by the filter processing unit 101 (to be referred to as a processed waveform example 102 hereinafter).

The nature waveform example 100 indicates, for example, a variation state when a sound of a flow of "wind" generated in nature is picked up by a microphone or the like for an arbitrary time. A factor such as "wind" is a pressure variation and has a frequency component. Therefore, a microphone for acoustic measurement, or the like generally measures pressure variations, and hence a pressure variation of, for example, "wind" is allowed to be measured by using a microphone or the like. Because of this, measurement by a microphone in nature can be referred to as "sound" measurement including "wind" measurement. When measurement is conducted, it is recognized that a variation state in nature is randomly changed as indicated by the nature waveform example 100.

The filter processing unit 101 functions to change characteristics such as a period or a peak level associated with the frequency characteristics of the nature waveform example 100. It is previously assumable that when there is a frequency band or a frequency component which coincides with or is approximate to an eigenvalue (known) of a housing (e.g., a housing 111 shown in FIG. 1) forming a home electrical appliance, a frequency component (of a sound) in nature and the eigenvalue of the housing of the home electrical appliance coincide with each other to generate noise/vibration.

Therefore, it is necessary to previously improve the characteristics in time axis at least to a minimum required degree such that each frequency component does not coincide with or is approximate to the eigenvalue. Acoustic processing required for an improvement at that time is filter processing for changing characteristics such as a period or a peak level. More specifically, in the filter processing, a frequency component of a temporal frequency variation characteristic of a sound generated in nature is suppressed and processed so as not to coincide with or be approximate to the eigenvalue of the housing of the facility apparatus provided with the driving part. Note that the filter processing may be performed either by filtering through a hardware filter circuit or by performing signal processing by means of software in advance. In addition, when a plurality of types of filter processing are performed, the accuracy of processing improves. As the filter processing, basic processing including LPF (low-pass filter), HPF (high-pass filter), BPF (band-pass filter), and the like is applicable to frequency characteristics, and envelope processing, flutter processing, processing of increasing/decreasing the required frequency, and the like are applicable to the entire temporal characteristics.

In the signal processing at that time, evaluation experiments for a subjective view and physiological response of users (humans) with respect to a sound in nature are performed for an unspecified number of humans by using an original temporal waveform of a sound in nature. In the subjective view evaluation experiment, an impression for a "sound" is clarified by using multivariate analysis such as the SD method (semantic differential method). In addition, in the physiological response evaluation experiment, a salivary amylase method having high correlation with a stress value, heart rate measurement, brain wave measurement, or the like is performed to determine an amount of sensing such as "pleasantness or unpleasantness" of humans with respect to an original "sound" in nature, and the amount of sensing is reflected on the information associated with the signal processing.

In subjective view evaluation, basically, a plurality of test sounds are presented to a subject, and he or she performs staged evaluation on an auditory impression obtained when directly hearing the presented test sounds, for a plurality of adjective pairs (e.g., pleasant-unpleasant) (called the SD method). Furthermore, an impression for the sound is allowed to be represented as a physical quantity by obtaining a contribution ratio for each adjective pair used for the evaluation of all the test sounds.

In physiological response evaluation, when a test sound is actually heard, an electrocardiogram, a heat rate, a brain wave, and the like are measured. In addition, after the sound is heard, a stress value or the like with respect to the test sound is measured by measuring salivary amylase or the like.

The processed waveform example 102 is a change in time axis waveform after results of the users' subjective view and physiological response evaluation experiments are reflected to improve the frequency band or the peak frequency component which coincides with or is approximate to the housing of the home electrical appliance. For example, a change component of relatively gentle wind of "wind" has great periodicity as a time axis variation and does not have a peak frequency component. A rapid change of, for example, gusty wind included in "wind" generates a waveform having sets of peaks and dips repeated in a short time (impulse characteristics), and its temporal pitch is naturally narrow.

A component having a relatively gentle time axis change is evaluated as "pleasant" in the subjective view and physiological response evaluation experiments, and, with a frequency variation of 100 Hz or lower, a sound pressure level factor is evaluated to be around 30 dB.

On the other hand, a component having a time axis change in a short time is evaluated as "unpleasant" in the subjective view and physiological response evaluation experiments, and with a frequency variation of 100 Hz or higher, a sound pressure level factor is evaluated to be 35 dB or higher.

That is, the pleasant sound making device A operates the driving part with a signal which is improved at least to a minimum required degree through the filter processing, an operation state of the driving part at that time is evaluated for a subjective view and physiological response of humans, selects a signal based on the variation characteristics obtained as a result of the filter processing, on the basis of the evaluation result, and generates a processed waveform example 102 used to operate the driving part based on the selected signal. Therefore, with the pleasant sound making device A, while the frequency band or the peak frequency component which coincides with or is approximate to the housing of the home electrical appliance is improved, the subjective view and physiological response evaluations of humans are reflected. Thus, it is possible to generate an acoustic characteristic which is determined as "pleasant" for humans.

The case where the processed waveform example 102 is used for the indoor unit 110 will be described.

The indoor unit 110 includes the housing 111, a fan 112, a motor portion 113, and a controller 115. The housing 111 forms an outer shell of the indoor unit 110, and the fan 112 and the motor portion 113 are housed in it. The fan 112 takes air in an air-conditioned area into the housing 111, and blows out air whose heat has been exchanged, into the air-conditioned area. The motor portion 113 drives the fan 112 by being controlled in rotation by the controller 115. The controller 115 drives the motor portion 113 on the basis of the processed waveform example 102 of the pleasant sound making device A. Note that although not shown, a heat exchanger and the like are also housed in the housing 111.

The controller 115 rotates the motor portion 113 on the basis of the input processed waveform example 102. As described above, in the processed waveform example 102, pitch adjustment is performed in time axis and a gentle sound pressure level which does not have a peak frequency component. Therefore, driving of the motor portion 113 is controlled to rotate so that wind approximate to gentle natural wind is blown out. Furthermore, in the processed waveform example 102, the results of the subjective view and physiological response evaluations of humans are reflected, and thus an unpleasant factor associated with rotation of the motor portion 113 is eliminated.

Note that in FIG. 1, the pleasant sound making device A and the controller 115 are separately shown, but the pleasant sound making device A may be provided as one function of the controller 115.

Figure 2:
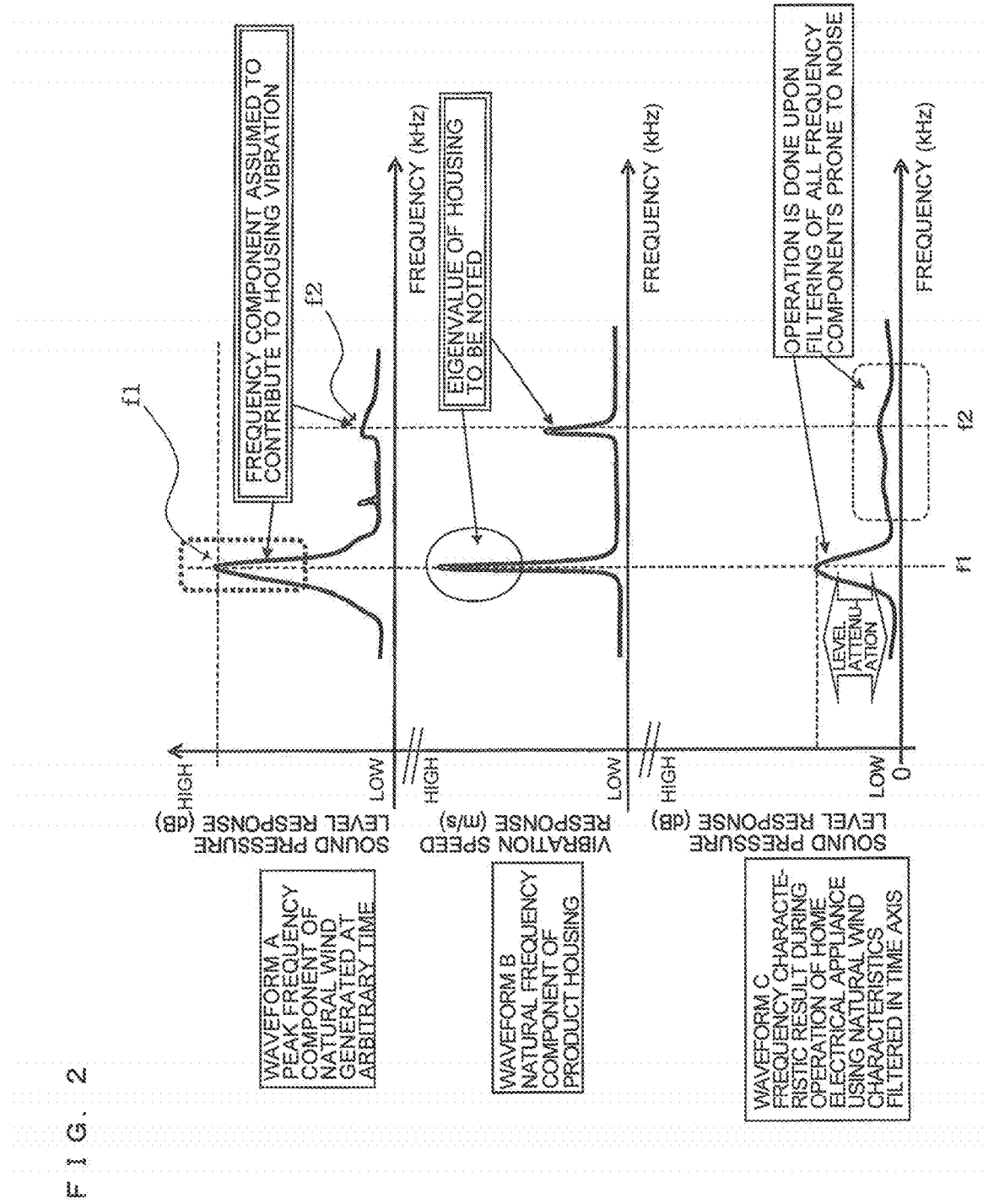
FIG. 2 is a conceptual diagram showing an example of a result of analysis of acoustic and vibration characteristics during the operation of an indoor unit.

FIG. 2 is a conceptual diagram showing an example of a result of analysis of acoustic and vibration characteristics during the operation of the indoor unit 110. The result of analysis of acoustic and vibration characteristics during the operation of the indoor unit 110 will be described with reference to FIG. 2. In FIG. 2, the abscissa indicates frequency (kHz), and the ordinate indicates sound pressure level response (db) in the upper part, vibration speed response (m/s) in the middle part, and sound pressure level response (db) in the lower part.

A waveform A shown in the upper part of FIG. 2 illustrates a frequency characteristic example obtained by average processing analysis of a temporal change in nature at arbitrary time, and has a peak frequency component f1 and a "wide frequency band" f2 having an arbitrary sound pressure level.

A waveform B shown in the middle part of FIG. 2 is a frequency characteristic example obtained by analyzing a natural vibration frequency of the housing 111 of the indoor unit 110, and, as an analysis result, has the peak frequency component f1 of the waveform A and a peak frequency component which coincides with the "wide frequency band" f2.

When the indoor unit 110 is operated in a frequency characteristic state of the waveform A, a housing vibration sound or a chattering sound of the housing which provides an "unpleasant" feeling to humans is generated so as to coincide with the eigenvalue of the housing 111 in the waveform B.

A waveform C shown in the lower part of FIG. 2 is obtained by filtering the waveform A. More specifically, in the waveform C, a result of subjective view and physiological response evaluations for "pleasant, unpleasant" for humans with respect to the waveform A is processed by the filter processing, and a peak frequency component or a frequency band which is evaluated as "unpleasant" is attenuated to a sound pressure level which is evaluated as "pleasant".

That is, when the pleasant sound making device A is used in the indoor unit 110, it is possible to operate the indoor unit 110 with the processed waveform example 102 supplied to the motor portion 113, an acoustic characteristic (noise characteristic) generated at that time becomes the waveform C, and it is possible to provide an acoustic characteristic which is always determined as "pleasant" by humans.

As described above, with the pleasant sound making device A, also in a facility apparatus in which a driving part such as a motor, a fan, or the like is rotated in accordance with a periodic signal and an unsteady signal which uses temporal variation characteristics in nature, it is possible to rotate the motor, the fan, or the like using a "pleasant sound making waveform" based on users' subjective view and physiological response evaluation results.

Embodiment 2

Figure 3:
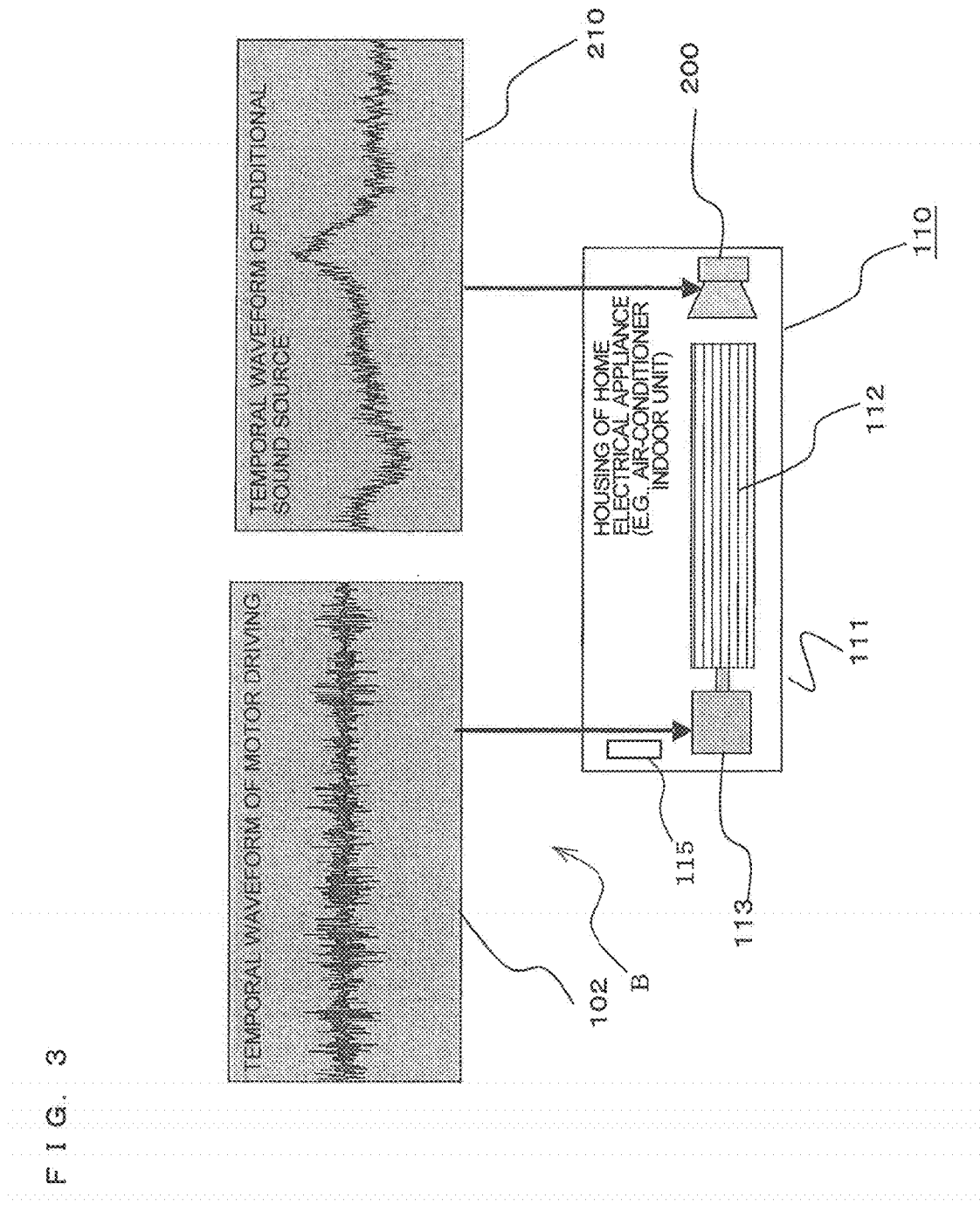
FIG. 3 is a schematic diagram for explaining an outline of a pleasant sound making device for a facility apparatus sound according to Embodiment 2 of the present invention.

FIG. 3 is a schematic diagram for explaining an outline of a pleasant sound making device for a facility apparatus sound (to be simply referred to as a pleasant sound making device B hereinafter) according to Embodiment 2 of the present invention. A case where the pleasant sound making device B is used in an indoor unit 110 of an air-conditioning apparatus which exemplifies a facility apparatus will be described herein as an example. The pleasant sound making device B makes noise generated during the operation of a home electrical appliance, into a pleasant sound, induces sleep, or induces a cool feeling or a warm feeling, for example, during air-conditioning operation. Note that in Embodiment 2, differences from Embodiments 1 will be mainly described, in which the same reference numerals denote the same parts as those in Embodiment 1, and a description thereof will be omitted.

The pleasant sound making device B has the configuration of the pleasant sound making device A according to Embodiment 1 as a basic configuration, and also includes a sound emission device 200 typified by a speaker or the like. In addition, the pleasant sound making device B is able to store a temporal waveform 210 for an additional sound source (to be referred to as an additional sound source waveform 210 hereinafter) supplied to the sound emission device 200. Although not shown, the pleasant sound making device B includes a filter processing unit 101 and is able to store the processed waveform example 102.

The sound emission device 200 is installed in an empty space of a housing 111 of the indoor unit 110. For example, in the indoor unit 110, the sound emission device 200 is preferably installed near an opening port through which air blown by the fan 112 is discharged. This is because when the sound emission device 200 is installed at such a position, it is possible to emit a sound to the fan 112. Thus, when the pleasant sound making device B is used, sounds generated by the fan 112 and the sound emission device 200 can be superimposed and emitted from the inside to the outside of the housing 111 of the home electrical appliance (the indoor unit 110 in the case of FIG. 3).

The additional sound source waveform 210 is generated using a sound in nature filtered on the basis of a temporal variation factor of the "heart rate" which is essential to the life rhythm of humans. The sound in nature is, for example, a "wave" or "wind", and the additional sound source waveform 210 is generated on the basis of their signal components, in particular, by using "fluctuation" of the signal components as a basis.

The processed waveform example 102 used to drive the motor portion 113 has been described in Embodiment 1. Therefore, since the operation of the motor portion 113 is controlled by the processed waveform example 102, a housing vibration sound generated irregularly is suppressed in the motor portion 113.

Under the motor operation environment, the pleasant sound making device B further uses an additional sound source waveform 210 for the sound emission device 200.

Figure 4:
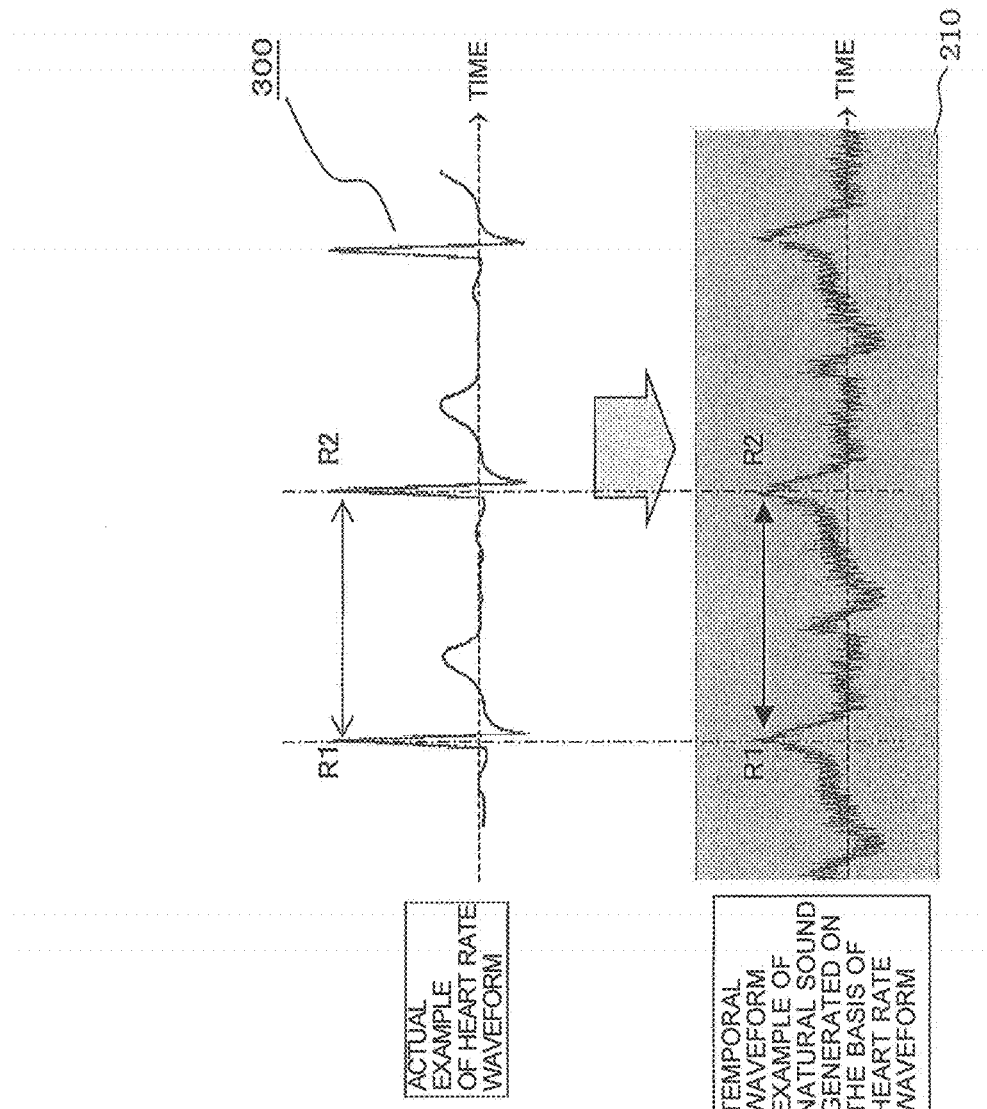
FIG. 4 is a schematic diagram for explaining an additional sound source waveform generated by the pleasant sound making device according to Embodiment 2 of the present invention.
Figure 5:
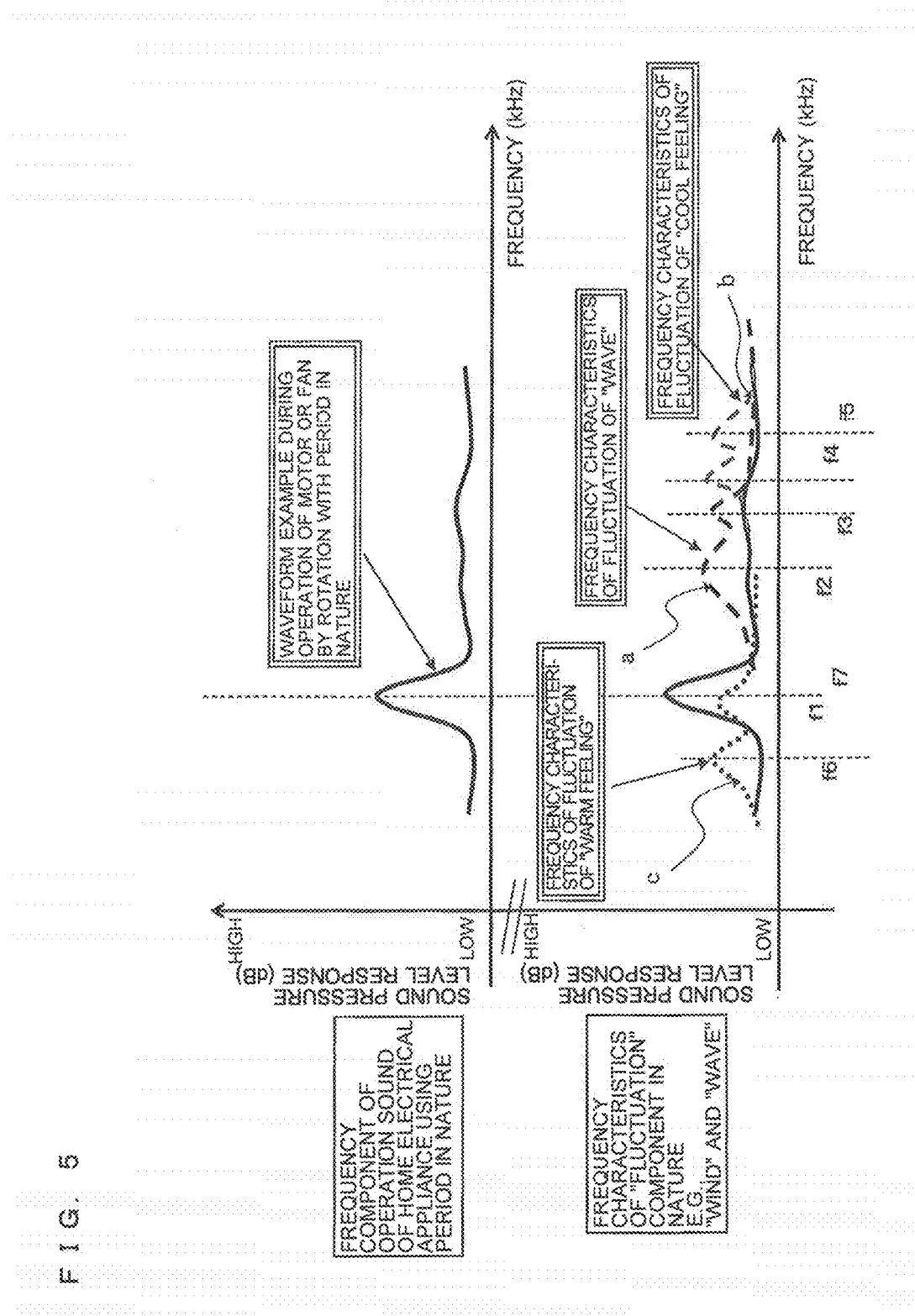
FIG. 5 is a conceptual diagram showing an example of frequency characteristics during the operation of the indoor unit.

FIG. 4 is a schematic diagram for explaining the additional sound source waveform 210 generated by the pleasant sound making device B. FIG. 5 is a conceptual diagram showing an example of frequency characteristics during the operation of the indoor unit 110. The additional sound source waveform 210 will be described in detail with reference to FIGS. 4 and 5. The upper part of FIG. 4 shows an actual heart rate waveform example 300 (to be referred to as an actual heart rate waveform example 300 hereinafter). The lower part of FIG. 4 shows the additional sound source waveform 210. In FIG. 5, the abscissa indicates frequency (kHz), and the ordinate indicates sound pressure level response (db) in both the upper and lower parts.

The actual heart rate waveform example 300 has a waveform corresponding to vibration generated by beating of the heart valves. As shown in FIG. 4, the actual heart rate waveform example 300 is determined as a low-stress, relaxed state, since parasympathetic nerve is predominant if the time interval between R1 and R2 is long to some extent. As will be described later, regarding a pitch interval of the voltage level of the additional sound source waveform 210, its superiority can be verified even through experimental verification by subjects. However, the average of the R1-R2 interval is 60 to 70 HR (HR: heart rate [BPM/min]), and it is known that an unpleasant factor is increased even if the heart rate is higher than the average or too low with respect to the average.

Thus, a sound pressure level and a period are adjusted with 60 to 70 HR, which is an average heart rate value, as a standard pitch of sound so as to obtain a rhythm of a sound. The intensity of the sound is applied as a "fluctuation" component to the additional sound source waveform 210 supplied to the sound emission device 200. A result of arbitrarily processing a temporal waveform of a natural sound such as "wind" or a "wave" by using a temporal variation of an average heart rate as mentioned above becomes the additional sound source waveform 210, which has characteristics as shown in FIG. 4. Note that in final adjustment of the additional sound source waveform 210, waveform selection is done such that the R1-R2 interval of the heart rate, which is subjective view and physiological response evaluation is 50 to 60 BPM, and a salivary amylase result is about 35 KU/L.

A frequency characteristic in an operation state of the home electrical appliance when the additional sound source waveform 210 is used is as shown in FIG. 5. A waveform with which the motor portion 113 or the fan 112 is operated to rotate at a period in nature from which an unpleasant factor has been removed is a solid line and has a gentle peak (f1). On the other hand, a frequency characteristic from the sound emission device 200 with the additional sound source waveform 210 is as indicated by a broken line a. This is because adjustment is performed on the basis of a "wave" sound and a so-called "fluctuation" period is provided by a heart rate or the like. The frequency characteristic tends to have two gentle peaks (f2 and f3). Thus, it is possible to reduce stress and cause, for example, sleep induction at bedtime.

A periodic variation is shortened (about 45 BPM), and two gentle peaks (f4 and f5) in a frequency band used for reproduction of the additional sound source are changed to a slightly high frequency band to provide "fluctuation" approximate to a steady sound such as a sound generated upon fall of water droplets, whereby it is possible to obtain a "cool feeling" (a broken line b).

On the other hand, a periodic variation is lengthened (about 90 BPM), and two gentle peaks (f6 and f7) are changed to a low frequency band, whereby it is possible to provide "fluctuation" approximate to a steady sound from, for example, a heater, so that a "warm feeling" can be obtained (broken line c).

Note that that f1 and f7 fall within almost the same band, but adjustment is performed for reproduction by setting the sound pressure level of f7 to be lower by about 5 dB than the sound pressure level of f1.

In the case where the pleasant sound making device B is used in a home electrical appliance such as an air-conditioner as described above, a "cool feeling" or a "warm feeling" can be provided only by sound without a forced temperature change, after temperature adjustment of the home electrical appliance is arbitrarily determined. Thus, the pleasant sound making device B attains energy saving for the operation of the home electrical appliance equipped with the pleasant sound making device B.

Note that the sound pressure level of a frequency characteristic which provides a gentle peak for the additional sound source is preferably provided as a level at which a sound of the additional sound source is hard to hear, such that reproduction is performed at a level lower by about 1 to 5 dB than the sound pressure level of a waveform (operation sound) used to operate a fan. By doing so, a dark noise operation is performed, and the same sound pressure level is outputted, thereby taking a countermeasure against a problem that a sound pressure from the additional sound source produces new stress with respect to humans.

As described above, with the pleasant sound making device B, similarly to the pleasant sound making device A, also in a facility apparatus in which a motor, a fan, or the like is rotated with a periodic signal and an unsteady signal which uses temporal variation characteristics in nature, it is possible to rotate the motor, the fan, or the like with a "pleasant sound making waveform" based on users' subjective view and physiological response evaluation results. In addition, with the pleasant sound making device B, it is possible to add, to a facility apparatus as a secondary signal, a pleasant sound making waveform which allows (A) a countermeasure against a housing vibration sound and (B) sleep induction, cool feeling adjustment, and warm feeling adjustment using a change in acoustic characteristic in time axis level. Furthermore, the pleasant sound making device B achieves energy saving for the operation of the home electrical appliance equipped with the pleasant sound making device B.

Embodiment 3

FIG. 6 is a schematic diagram for explaining an outline of a pleasant sound making device for a facility apparatus sound (to be simply referred to as a pleasant sound making device C hereinafter) according to Embodiment 3 of the present invention. A case where the pleasant sound making device C is used in an indoor unit 110 of an air-conditioning apparatus which exemplifies a facility apparatus will be described herein as an example. The pleasant sound making device C makes noise generated during the operation of a home electrical appliance, into a pleasant sound, induces sleep, or induces a cool feeling or a warm feeling, for example, during air-conditioning operation. Note that in Embodiment 3, differences from Embodiments 1 and 2 will be mainly described, in which the same reference numerals denote the same parts as those in Embodiments 1 and 2, and a description thereof will be omitted.

As shown in FIG. 6, the indoor unit 110 includes a flap 400 for blowing air from the indoor unit 110 in an arbitrary direction. The flap 400 is provided at an air outlet of the housing 111.

The pleasant sound making device C has the configurations of the pleasant sound making device A according to Embodiment 1 and the pleasant sound making device B according to Embodiment 2 as a basic configuration, and also includes one or more small-sized sound emission devices 410 provided in a space within the indoor unit 110 at its end portion, and an acoustic circuit portion 420 including a modulator for driving the small-sized sound emission devices 410.

The small-sized sound emission devices 410 are formed from a piezoelectric material such as PZT capable of ultrasonic emission. When ultrasonic emission devices are used as the small-sized sound emission devices 410, it is possible to reduce the sizes and the thicknesses of the small-sized sound emission devices 410. Thus, a space to install the indoor unit 110 including the pleasant sound making device C need not have a large capacity, which makes the indoor unit 110 compact. The small-sized sound emission devices 410 are installed to be able to perform "sound emission" in parallel to the longitudinal direction of the flap 400. The small-sized sound emission devices 410 are able to perform linear sound emission relative to the lateral direction (widthwise direction from the right to the left) within the housing 111.

The acoustic circuit portion 420 causes the small-sized sound emission devices 410 to perform linear sound emission. The acoustic circuit portion 420 includes a signal generation portion 421, a modulation portion 422, and an oscillation circuit portion 423 for oscillating a frequency equal to the resonant frequencies of the small-sized sound emission devices 410. That is, linear sound emission of the small-sized sound emission devices 410 is executed by three components, namely, the signal generation portion 421, the modulation portion 422, and the oscillation circuit portion 423. Furthermore, the signal generation portion 421 of the acoustic circuit portion 420 includes "sound source data" controlled with an arbitrary frequency band and rhythm based on physiological response evaluation by a natural sound which makes it possible to reduce stress, induce sleep, or provide a cool feeling or a warm feeling for humans.

For example, if the small-sized sound emission devices 410 are able to generate a sound in the ultrasonic band by resonation at a frequency of 30 kHz, the oscillation circuit portion 423 of the acoustic circuit portion 420 generates an oscillation frequency of 30 kHz. The oscillation frequency of 30 kHz is superimposed on (added to) a signal from the signal generation portion 421 of the acoustic circuit portion 420 by the modulation portion 422 of the acoustic circuit portion 420. The signal from the signal generation portion 421 of the acoustic circuit portion 420, which includes the "sound source data", is superimposed on (added to) a signal in the ultrasonic band from the oscillation circuit portion 423 of the acoustic circuit portion 420 by the modulation portion 422 of the acoustic circuit portion 420.

Then, the sum signal is emitted by the small-sized sound emission devices 410 into the housing 111. The emitted signal is repeatedly emitted and reflected between the small-sized sound emission devices 410 and a surface opposed to the small-sized sound emission devices 410. By doing so, a "wall" of a sound generated by linear sound emission is formed between the fan 112 and the flap 400 (an arrow P shown in FIG. 6). A noise-containing sound from the fan 112 is shielded by masking of the "wall of sound" formed by the signal emitted by the small-sized sound emission devices 410, and air itself from the fan 112 can be blown through the flap 400 to the outside of the housing 111.

Furthermore, in reflection at the surface opposed to the small-sized sound emission devices 410, the modulated sound is demodulated to generate a demodulated sound at the reflection surface and in its vicinity. As a result of demodulation, a "sound" is generated in nature upon filter processing, so that a "sound" is generated by an arbitrary signal from the acoustic circuit portion 420 and propagates from the inside of the housing 111 to the outside of the housing 111. That is, a sound is emitted for sleep induction or providing a cool feeling or a warm feeling, and the sound is emitted from the outside of the housing 111 to a human simultaneously with air blown by the fan 112.

As described above, with the pleasant sound making device C, similarly to the pleasant sound making devices A and B, also in a facility apparatus in which a motor, a fan, or the like is rotated with a periodic signal and an unsteady signal which uses temporal variation characteristics in nature, it is possible to rotate the motor, the fan, or the like with a "pleasant sound making waveform" based on users' subjective view and physiological response evaluation results. In addition, with the pleasant sound making device C, it is possible to add, to a facility apparatus as a secondary signal, a pleasant sound making waveform which allows (A) a countermeasure against a housing vibration sound and (B) sleep induction, cool feeling adjustment, and warm feeling adjustment using a change in acoustic characteristic in time axis level. Furthermore, with the pleasant sound making device C, it is possible to blow out wind itself, and simultaneously with this, it is possible to perform sound emission for sleep induction or providing a cool feeling or a warm feeling.

Embodiments 1 to 3 have been described based on the indoor unit 110 of the air-conditioner as an application example of the pleasant sound making device according to the present invention, but the pleasant sound making device according to the present invention is not limited to that applied to the indoor unit 110 of the air-conditioner. For example, the pleasant sound making device according to the present invention is applicable to home electrical appliances which generate sounds, including other air-conditioning apparatuses or cleaners, and apparatuses other than home electrical appliances, for example, apparatuses having a problem with an inverter sound. If the pleasant sound making device according to the present invention is applied to such an apparatus, it is possible to make noise produced by the product into a pleasant sound by reproducing a sound with a temporal waveform for an additional sound source based on subjective view and physiological response evaluations.

In addition, in Embodiments 1 to 3, a characteristic tendency with respect to a certain age group is shown, but the frequency band of the additional sound source is influenced by auditory characteristics that depend on the age. Thus, the pleasant sound making device according to the present invention is able to move (change) the frequency band, in which reproduction of the additional sound source is performed in accordance with aging, to the low frequency band side in accordance with an age group. For example, the movement may be able to be arbitrarily selected by inputting an age with a remote control or the like which controls the home electrical appliance.

REFERENCE SIGNS LIST 100 time axis-input voltage waveform example of sound in nature 101 filter processing unit 102 time axis-input voltage waveform example
110 indoor unit 111 housing 112 fan 113 motor portion
115 controller 200 sound emission device 210 temporal waveform for additional sound source 300 actual example of heart rate waveform
400 flap 410 small-sized sound emission device 420 acoustic circuit portion 421 signal generation portion 422 modulation portion
423 oscillation circuit portion A pleasant sound making device for facility apparatus sound B pleasant sound making for device facility apparatus sound C pleasant sound making device for facility apparatus sound

The invention claimed is:

1. A pleasant sound making device for a facility apparatus sound which makes a sound generated by a facility apparatus which operates a driving part which is a fan or a motor of the facility apparatus, into a pleasant sound, the pleasant sound making device comprising:
   a filter processing unit, the filter processing unit is configured to:
      suppress a portion of a frequency component of a temporal variation characteristic of a frequency of a sound existing in nature, which coincides with or is approximate to an eigenvalue of a housing of the facility apparatus provided with the driving part which is the fan or the motor of the facility apparatus, and
   a signal processing unit, the signal processing unit is configured to:
      select, in advance based on evaluation results of a subjective view and physiological response of humans with respect to the sound existing in nature when the driving part is operated, a signal obtained by the filter processing unit that suppresses the portion of the frequency component of the temporal variation characteristic of the frequency of the sound existing in nature, which coincides with or is approximate to the eigenvalue of the housing of the facility apparatus provided with the driving part, and
      generate an operation signal based on the selected signal, and control the operation signal to drive the driving part which is the fan or the motor of the facility apparatus based on the selected signal.

2. The pleasant sound making device for a facility apparatus sound of claim 1, further comprising
   a sound emission device disposed inside the housing of the facility apparatus, wherein
   the sound emission device includes a speaker or an ultrasonic emitter formed of a piezoelectric material, the sound emission device emits a sound obtained by adjusting a sound pressure level and a period of the sound in nature using an average heart rate of the humans.

3. The pleasant sound making device for a facility apparatus sound of claim 2, wherein a sound pressure level of the sound emitted by the sound emission device is lower by about 1 to 5 dB than a sound pressure level of an operation sound generated when the driving part is operated.

4. The pleasant sound making device for a facility apparatus sound of claim 2,
wherein the sound emission device further includes:
a signal generation portion including sound source data obtained by performing predetermined signal processing on the sound in nature;
an oscillation circuit portion which drives the sound emission device in an ultrasonic band; and
a modulation portion which superimposes a signal from the signal generation portion on a signal in the ultrasonic band from the oscillation circuit portion.

5. The pleasant sound making device for a facility apparatus sound of claim 4, wherein
the driving part, which is driven by the operation signal generated by the signal processing unit, comprises a fan,
an air outlet is formed in the housing,
the sound emission device is installed at one end portion of the housing across the air outlet, and
the sound emitted by the sound emission device is repeatedly emitted and reflected between the sound emission device and another end portion of the housing opposite to the sound emission device, to form a wall of a sound.

6. The pleasant sound making device for a facility apparatus sound of claim 5,
wherein a sound which is modulated by the modulation portion and emitted by the sound emission device is demodulated and reproduced as a sound at the other end portion of the housing opposite to the sound emission device.

7. The pleasant sound making device for a facility apparatus sound of claim 4, wherein a band of a frequency characteristic of the sound generated by the sound emission device is changeable in accordance with an age group.

8. A pleasant sound making method for a facility apparatus, the pleasant sound making method for making a sound generated by a facility apparatus which operates a driving part which is a fan or a motor of the facility apparatus, into a pleasant sound, the pleasant sound making method comprising:
suppressing and processing, by filter processing of a pleasant sound making device, a portion of a frequency component of a temporal variation characteristic of a frequency of a sound existing in nature, which coincides with or is approximate to an eigenvalue of a housing of the facility apparatus provided with the driving part;
evaluating, by the pleasant sound making device, a signal based on the processed variation characteristic of the frequency processed by the filter processing, based on evaluation results of a subjective view and physiological response of humans with respect to a sound existing in nature when the driving part is operated;
selecting, by the pleasant sound making device, the signal based on the processed variation characteristic of the frequency based on the evaluation results of the subjective view and physiological response of the humans;
generating, by the pleasant sound making device, an operation signal based on the selected signal;
controlling, by the pleasant sound making device, the operation signal to drive the driving part which is the fan or the motor of the facility apparatus based on the selected signal; and
emitting, by the pleasant sound making device, as an additional sound source, during operation of the facility apparatus, a sound obtained in advance by adjusting a sound pressure level and a period of the sound in nature with an average heart rate of humans.

9. The pleasant sound making device for a facility apparatus sound of claim 3,
wherein the sound emission device further includes:
a signal generation portion including sound source data obtained by performing predetermined signal processing on the sound in nature;
an oscillation circuit portion which drives the sound emission device in an ultrasonic band; and
a modulation portion which superimposes a signal from the signal generation portion on a signal in the ultrasonic band from the oscillation circuit portion.

10. The pleasant sound making device for a facility apparatus sound of claim 5,
wherein a band of a frequency characteristic of the sound generated by the sound emission device is changeable in accordance with an age group.

11. The pleasant sound making device for a facility apparatus sound of claim 6,
wherein a band of a frequency characteristic of the sound generated by the sound emission device is changeable in accordance with an age group.

12. The pleasant sound making device for a facility apparatus sound of claim 1,
wherein the subjective view and physiological response of the humans include an auditory impression on the subject when the subject hears a plurality of test sounds, and a physiological response of the subject when the subject hears an actual test sound.

13. A facility apparatus comprising:
a driving part; and
the pleasant sound making device for a facility apparatus sound of claim 1.

14. The facility apparatus of claim 13, wherein the driving part is at least one of a motor and a fan.

15. The pleasant sound making device for a facility apparatus sound of claim 1, wherein
the filter processing unit includes a hardware filter circuit.

16. The pleasant sound making device for a facility apparatus sound of claim 1, further comprising
a controller of the facility apparatus,
wherein the driving part is housed in the housing of the facility apparatus,
wherein the controller is configured to drive the driving part based on the operation signal.

17. The pleasant sound making device for a facility apparatus sound of claim 15, further comprising
a controller of the facility apparatus,
wherein the driving part is housed in the housing of the facility apparatus,
wherein the controller is configured to drive the driving part based on the operation signal.

* * * * *